US012137896B2

(12) United States Patent  
Liu

(10) Patent No.: US 12,137,896 B2  
(45) Date of Patent: Nov. 12, 2024

(54) SUTURING APPARATUS WITH KNOTTING TUBE USING AUTOTRANSFER AND METHOD THEREOF

(71) Applicant: Children's Medical Center Corporation, Boston, MA (US)

(72) Inventor: Kaifeng Liu, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 1115 days.

(21) Appl. No.: 16/647,300

(22) PCT Filed: Sep. 12, 2018

(86) PCT No.: PCT/US2018/050616  
§ 371 (c)(1),  
(2) Date: Mar. 13, 2020

(87) PCT Pub. No.: WO2019/055484  
PCT Pub. Date: Mar. 21, 2019

(65) Prior Publication Data  
US 2020/0214695 A1 Jul. 9, 2020

Related U.S. Application Data

(60) Provisional application No. 62/558,665, filed on Sep. 14, 2017.

(51) Int. Cl.  
*A61B 17/04* (2006.01)  
*A61B 17/00* (2006.01)  
*A61B 17/06* (2006.01)

(52) U.S. Cl.  
CPC .... *A61B 17/0469* (2013.01); *A61B 17/06004* (2013.01); *A61B 2017/00876* (2013.01);  
(Continued)

(58) Field of Classification Search  
CPC .......... A61B 17/0469; A61B 17/06004; A61B 2017/00876; A61B 2017/0474;  
(Continued)

(56) References Cited

U.S. PATENT DOCUMENTS 5,722,981 A  3/1998  Stevens  
9,089,262 B2 * 7/2015  Hashiba ................ A61B 1/018  
(Continued)

FOREIGN PATENT DOCUMENTS

WO  2011/025767 A1  3/2011

*Primary Examiner* — Sarah W Aleman  
*Assistant Examiner* — Mikail A Mannan  
(74) *Attorney, Agent, or Firm* — GREENBERG TRAURIG, LLP

(57) ABSTRACT

A suturing system and a method thereof are provided. The suturing system includes a tube that has a first rod moveable therein and a second rod that is coupled to an outer surface of the tube. A needle is coupled to an end of the tube and includes an insertion portion. In addition, a suture lock is inserted onto the second rod and a first end of a suture engages with a tip of the needle or the tube. A second end of the suture is fixed within the suture lock. The insertion portion is engaged with the first end of the suture prior to insertion through the material. The suturing system allows for single handed operation, thus simplifying a suturing process while improving accuracy.

18 Claims, 16 Drawing Sheets

(52) U.S. Cl.
CPC ............... *A61B 2017/0474* (2013.01); *A61B 2017/0488* (2013.01); *A61B 2017/06009* (2013.01); *A61B 2017/06042* (2013.01)

(58) Field of Classification Search
CPC .. A61B 2017/0488; A61B 2017/06009; A61B 2017/06042; A61B 2017/0608; A61B 17/0487; A61B 17/04; A61L 17/00
See application file for complete search history.

(56) References Cited

U.S. PATENT DOCUMENTS

| | | |
|---|---|---|
| 2012/0109196 A1 | 5/2012 | McCaw et al. |
| 2015/0100071 A1 | 4/2015 | Phillips et al. |
| 2018/0042608 A1* | 2/2018 | Dumanian ....... A61B 17/06066 |

* cited by examiner

SUTURING APPARATUS WITH KNOTTING TUBE USING AUTOTRANSFER AND METHOD THEREOF

CROSS-REFERENCE TO RELATED APPLICATIONS

This application is a National Phase application filed under 35 USC 371 of PCT International Application PCT/US2018/050616 with an International Filing Date of Sep. 12, 2018, which claims priority from U.S. Provisional Application No. 62/558,665, filed on Sep. 14, 2017. The entire contents of these applications are incorporated herein by reference in their entirety.

TECHNICAL FIELD

The present disclosure relates generally to a suturing apparatus with a knotting tube, and more particularly, to a suturing apparatus that uses autotransfer to perform suturing and includes a suture lock to secure the suture against a material.

BACKGROUND

In general, stitching or suturing, in a medical field, are techniques used to bind pieces of material together. Specifically, suturing is used to stitch together pieces of tissue during a surgical procedure. The pieces of tissue will then fuse together during a healing process. A suture needle is typically used to force a suture thread through the layers of tissue to allow the thread to bind the tissue layers. That is, the suture is looped through the needle and is then passed in and out of a surgical site to close the wound. Such a procedure requires accurate manipulation and requires the application of sufficient tension to secure the suture against the surgical site.

A typical suture needle includes a needle tip at one end and a suture connection point at the other end. The tip of the needle is inserted through a material by applying insertion force to the suture needle. Additional force is then required to guide the remainder of the needle through the material until the entire needle is passed therethrough. The process of inserting the needle with the suture thread through the material or tissue is then repeated to close the wound. This stitching process, however, typically requires the use of a pair of tweezers to grip a portion of the suture needle and pull it through the material. A recently developed technology uses a roller to push the needle through the material. That is, the needle is rolled through the holder which minimizes the force required to push the needle through the material. However, this technology does not provide a mechanism for returning the needle to the rollers to continue the stitching process. Thus, a user is still required to manually assist the process.

Another developed technology includes a pair of tweezers that house the suture needle between the tips of the tweezers. In particular, a straight double-ended suture needle is movable between the tips of the tweezers upon engagement of the tweezers. For example, when a user squeezes the tweezer arms together, the suture needle disconnects from one tip and engages with the other tip. This design also reduces the need to push the needle itself to puncture through a material. However, this design requires multiple interworking elements within the tweezer arms to lock the needle end in place, thus increasing risk of use error.

The above-described stitching technologies also require a separate process of knotting the end of the suture to secure the suture against the surgical site. Human error may cause insufficient tension to be applied to such a knot, resulting in less accuracy in the closing of a wound. The traditional knot tying technique is time consuming and requires extensive training for medical professionals to be capable of accurately securing the suture to a surgical site. Various techniques have been researched for improving the accuracy of these medical procedures, such as for example, a clip applied to the ends of the suture. However, such a technique is limited in application due to the size thereof and difficult of manipulation near the tissue or other material. Thus, such a technique would not be capable of being applied against a surgical site with sufficient tension to accurately close the wound. Accordingly, to further improve the procedures related to suturing and binding of materials, it is necessary to provide a device that decreases the training time of suturing and knot tying while increasing the accuracy and simplicity of the process.

SUMMARY

The present disclosure provides a suturing apparatus that uses autotransfer to perform suturing and includes a knotting tube to bind and lock the suture against a material.

According to one aspect of the present disclosure a suturing system is provided that includes a tube having a first rod movable therein and a second rod coupled to an outer surface of the tube. A needle having an insertion portion is coupled to an end of the tube and a suture lock is inserted onto the second rod. A first end of a suture engages with a tip of the needle or the tube and a second end of the suture is fixed within the suture lock. The insertion portion is also engaged with the first end of the suture prior to insertion through a material.

Furthermore, the suture lock may include a knotting tube having a passageway formed therethrough and a plurality of protrusions extending from at least a portion of an inner surface of the knotting tube to pierce the suture. The suture lock may then be moved to abut a surgical site. The protrusions are deformable in one direction to fix the suture and maintain the knotting tube abutting the surgical site.

In an exemplary embodiment, the suture is magnetically engaged with the tip of the needle or the tube. The first end of the suture may be magnetic, the first rod within the tube may be magnetic, and the second rod coupled to the outer surface of the tube may be magnetic. The magnetic strength of the first rod may be greater than the magnetic strength of the first end of the suture. The first rod and the second rod have a same magnetic field direction and the first rod and the first end of the suture have an opposite magnetic field direction.

In addition, the first rod may then be pushed toward the end of the tube to release the first end of the suture from the tip of the needle and allow engagement with the end of the tube. The first rod may then be retracted into the tube to release the first end of the suture from the end of the tube and allow engagement with the second rod. The suturing system may be pulled away from a surgical site to allow the first end of the suture to pass through the suture lock and fix the suture against the surgical site. The movement of the first rod may be controlled by a lever integrally formed on the tube.

According to another aspect of the present disclosure, a suturing method is provided that includes engaging a second end of a suture with a suture lock coupled to an outer surface of a tube having a first rod movable therein. A first end of the suture may be engaged with a tip of a needle coupled to an end of the tube. The method may further include piercing an insertion portion of the needle and the first end of the suture through a material. The first rod may then be pushed toward the end of the tube to release the first end of the suture from the needle and to engage the first end of the suture with the end of the tube. Further, the first rod may be retracted back into the tube to engage the first end of the suture with a second rod on which the suture lock is disposed and the first end of the suture may be pulled through the suture lock to fix the suture against the material.

Notably, the present disclosure is not limited to the combination of suturing apparatus elements as listed above and may be assembled in any combination of the elements as described herein.

Other aspects of the disclosure are disclosed infra.

BRIEF DESCRIPTION OF THE DRAWINGS

The embodiments herein may be better understood by referring to the following description in conjunction with the accompanying drawings in which the like reference numerals indicate identically or functionally similar elements, of which.

Figure 1:
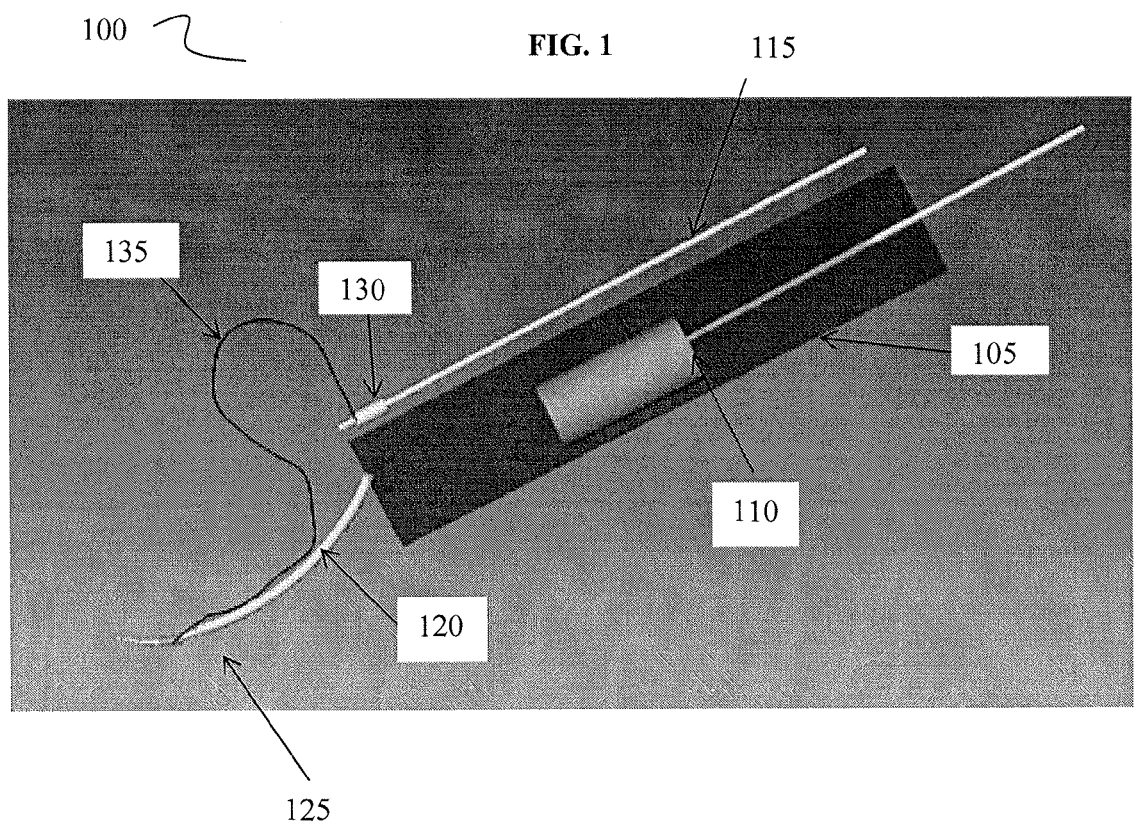
FIG. 1 illustrates a suturing system according to an exemplary embodiment of the present disclosure.

It should be understood that the appended drawings are not necessarily to scale, presenting a somewhat simplified representation of various features illustrative of the basic principles of the disclosure. The specific design features of the present disclosure as disclosed herein, including, for example, specific dimensions, orientations, locations, and shapes will be determined in part by the particular intended application and use environment.

LIST OF REFERENCE NUMERALS

105: tube
110: first rod
115: second rod
120: needle
125: insertion portion
130: suture lock
135: suture
140: material
145: ring-shaped magnet
205: knotting tube
210: protrusions
305: forceps arm
310: guiding loop

DETAILED DESCRIPTION

The present disclosed subject matter will be described more fully hereinafter with reference to the accompanying drawings, in which some, but not all embodiments of the disclosure are shown. The presently disclosed subject matter may be embodied in many different forms and should not be construed as limited to the embodiments set forth herein; rather these exemplary embodiments are provided so that this disclosure will satisfy applicable legal requirements. Indeed, many modifications and other exemplary embodiments of the presently disclosed subject matter set forth herein will come to mind to one skilled in the art to which the presently disclosed subject matter pertains, having the benefit of the teachings presented in the foregoing descriptions the associated drawings. Therefore, it is to be understood that the presently disclosed subject matter is not limited to the specific embodiments disclosed and that modifications and other exemplary embodiments are intended to be included within the scope of the appended claims.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

In one aspect, the present disclosure provides a suturing system that uses autotransfer of a suture thread between a needle and a tube while also incorporating a suture lock that fixes the suture against a surgical site. The suturing system thus not only simplifies the suturing process and decreases the amount of time required for suturing but also simplifies the knot tying process at the end of the suturing process thus ensuring a more seamless complete process. The system generally simplifies the suturing process by allowing the system to be operated single-handedly. Accordingly, a surgeon or other type of user has the ability to have improved control and use the free hand for other tasks such as holding another instrument without requiring the aid of an assistant. Additionally, a user of the system is not required to manually pull the entire needle through a material or tissue since the suture thread automatically passes between the needle tip and the tube. In other words, one end of the suture is engaged with the tip of the needle and once the insertion portion thereof is pierced through the material, the suture end is transferred to the tube end. The suture end is held at the tube end while the needle tip re-pierces the material. This allows the user to place stitches in typically inaccessible locations or areas with substantial spatial constraints.

In surgical applications, the suture may be a suture thread designed for use with organic tissue and may be composed of an absorbable or non-absorbable material. For example, the thread may be composed of an absorbable material such as catgut, polyglycolic acid, polyactic acid, polydioxanone, caprolactone, and the like. Exemplary non-absorbable materials include polypropylene, polyester, nylon, metallic wires, and the like. In some cases, the thread may be coated with a compound that reduces friction during the suturing process, has antibacterial properties, and/or produces a biological reaction in the subject of the procedure (e.g., acts as an anti-inflammatory, etc.). However, the suturing system of the present disclosure is not limited to surgical applications. The suturing system may be applied to various other fields in which two or more materials are being bound together. For example, the system may be applied to a packaging field in which minimally sized packaging materials require a binding process. Herein below the system will be described in relation to a surgical application as an example with the understanding that the present disclosure is not limited thereto.

Referring to FIG. 1, a suturing system 100 is shown according to an exemplary embodiment of the present disclosure. In particular, the suturing system 100 may include a tube 105 having a first rod 110 movable therein. A second rod 115 may be coupled to an outer surface of the tube 105. In particular, the second rod 115 may extend at least along a portion of the outer surface of the tube 105 but is not required to extend the entire length thereof. Further, a needle 120 is coupled to an end of the tube 105. The needle 120 may specifically include an insertion portion 125 used to pierce through a material. As previously discussed, the entire length of the needle 120 is not required to pierce through the material due to the automatic transfer of the suture as described herein below in further detail.

In addition, the suturing system includes a suture lock 130 inserted onto the second rod 115. The suture lock 130 will be described in further detail herein below. A first end of a suture 135 engages with a tip of the needle 120 or the tube 105 (e.g., an end of the tube) and a second end of the suture 135 is fixed within the suture lock 130. The system configuration as described above allows for the insertion portion 125 of the needle 120 to be engaged with the first end of the suture 135 prior to insertion through a material 140 (e.g., tissue) as shown in FIG. 2.

According to an exemplary embodiment of the present disclosure, the suture 135 may be magnetically engaged with the tip of the needle 120 or the tube 105. In particular, the first end of the suture 135 may be magnetic, the first rod 110 within the tube 105 may be magnetic, and the second rod 115 coupled to the outer surface of the tube 105 may be magnetic. Alternately, a ring shaped magnet may be attached at the first end of the suture provide the magnetic connection. Such a feature will be described in further detail below. Further, the magnetic strength of the first rod 110 may be greater than a magnetic strength of the first end of the suture 135. The first rod 110 and the second rod 115 may have a same magnetic field direction and the first rod 110 and the first end of the suture 135 may have an opposite magnetic field direction. Based on these magnetic relations, a discussion will now be provided regarding the operation of the suturing system.

Figure 2:
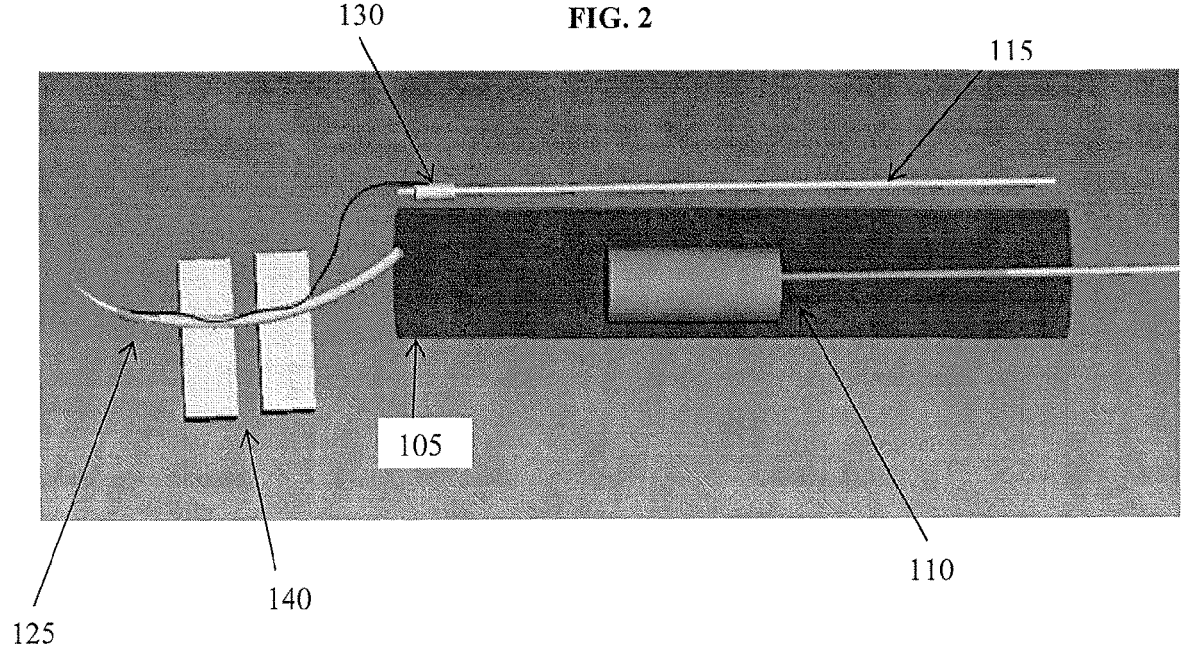
FIG. 2 illustrates the suturing system engaging with a material according to an exemplary embodiment of the present disclosure.
Figure 3:
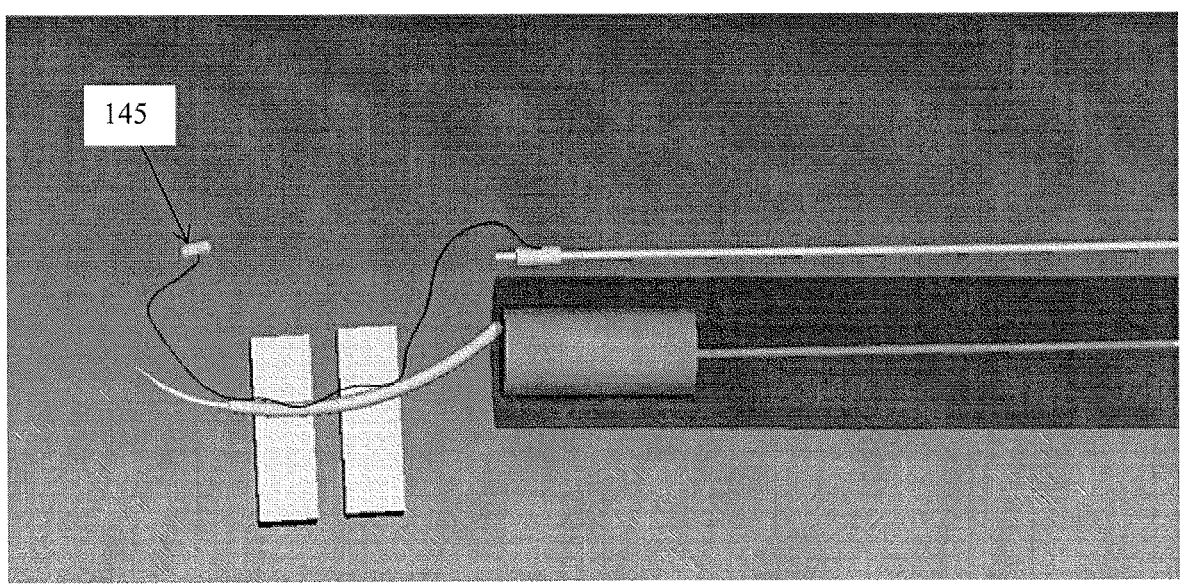
FIG. 3 illustrates one end of a suture being repelled from a needle tip according to an exemplary embodiment of the present disclosure.

Referring to FIG. 2, the first end of the suture 135 and the insertion portion 125 of the needle 120 are pierced through a material 140 to begin the suturing process. The type of material may vary based on the application of the suturing system 100. For example, in a surgical application the material may be tissue. Once the insertion portion 125 and suture 135 have pierced through the material 140, the first rod 110 within the tube 105 may be pushed toward the end of the tube at which the needle 120 is coupled, as shown in FIG. 3. Due to the magnetic field directions of the components as described above, the movement of the first rod 110 toward the end of the tube 105 releases the first end of the suture 135 from the tip of the needle 120 and allows for engagement with the end of the tube 105 as shown in FIG. 4.

Figure 4:
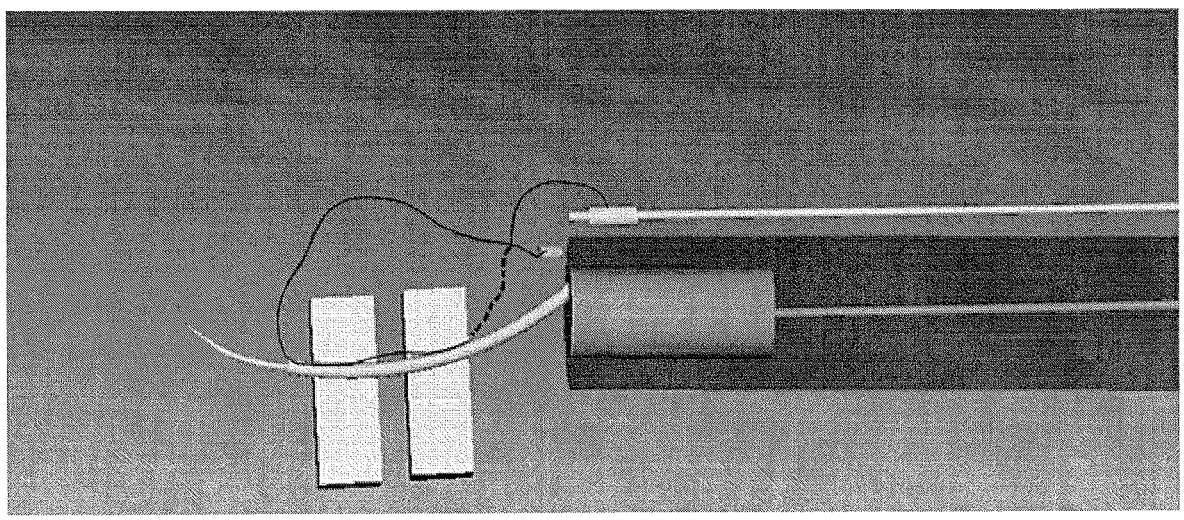
FIG. 4 illustrates the suture end being attracted to the tube of the suturing system according to an exemplary embodiment of the present disclosure.

In particular, the first rod 110 is moved in the left direction of FIG. 4 toward the end of the tube 105 and the magnetic field of the first rod 110 is thus close to the first end of the suture 135. The magnetic field increases as the first rod 110 moves closer to the end of the tube 105, thus increasing the attraction to the first end of the suture 135. The first end of the suture 135 is then repelled off the tip of the needle 120 by the increased magnetic field from the first rod 110 (which is different magnetic field direction from the first end of the suture) and engages with the end of the tube 105. During the transition from the tip of the needle to the end of the tube, the first end of the suture may rotate, causing the magnetic field direction thereof to be the same as that of the first rod. In particular, when the first end of the suture 135 is engaged with the tip of the needle 120, the magnet component at the first end of the suture 135 is unable to rotate due to the engagement with the tip of the needle 120. However, when the first end of the suture 135 is repelled off the tip of the needle 120, it is free to rotate to the same magnetic field direction as the first rod 110. For example, the magnetic component may rotate about 180 degrees and then the magnetic field direction thereof becomes the same as that of the first rod 110.

Figure 16:
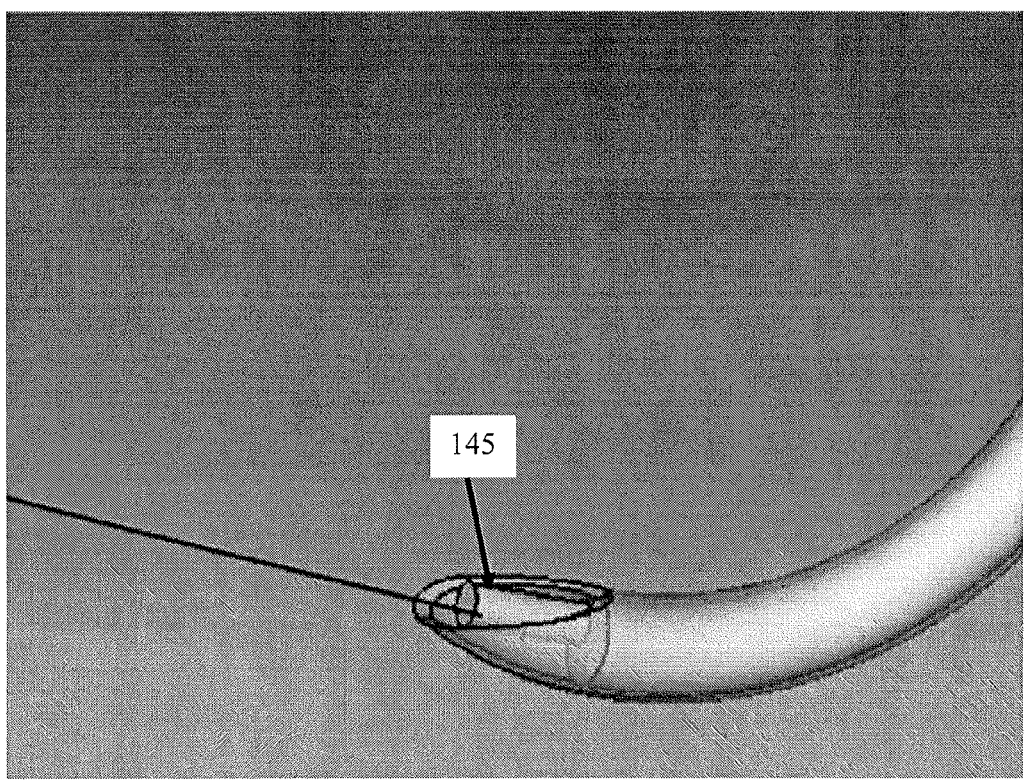
FIG. 16 illustrates a ring-shaped magnet engaged with the suture and inserted into a needle tip according to another exemplary embodiment of the present disclosure.

At this point, the suture has been inserted through the material and has made a loop over the material after engaging with the end of the tube. Accordingly, to continue the suturing process, the system may be pulled back such that the insertion portion of the needle is capable of being re-pierced through the material again. This process may be repeated until the desired number of stitches has been added to the surgical site. In addition, as shown in FIG. 3, the first end of the suture that engages with the tip of the needle in the tube (e.g., the end that is not fixed within the suture lock) may be in the form of a ring-shaped magnet 145. However, the present disclosure is not limited to such a particular size and the end of the suture may be any shape or form. For example, the shape could be a hollow cone shape, an elongated tubular structure, or the like. The end of the suture may also be a separate component from the suture or may be formed integrally therewith. As shown in FIG. 16, the tip of the needle may also be of a varied shape. For example, as shown in the figure, the tip of the needle may have an opening capable of accommodating the magnet 145 discussed above to thus engage with the suture. Alternately, the tip of the needle may be a closed tapered tip, but the present disclosure is not limited thereto.

Figure 5:
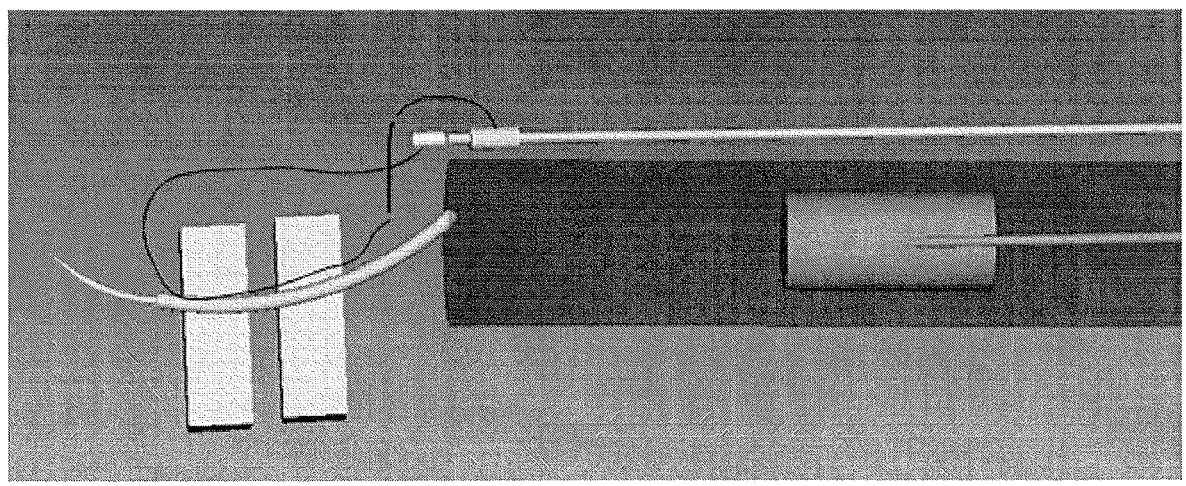
FIG. 5 illustrates the suture end being attracted to the rod on which a suture lock is disposed according to an exemplary embodiment of the present disclosure.
Figure 6:
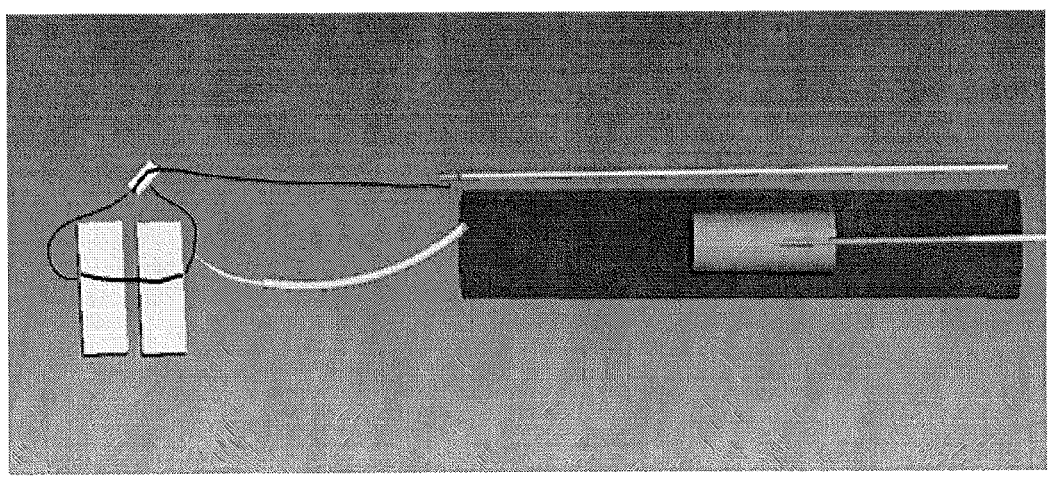
FIG. 6 illustrates the locking of the suture against a material according to an exemplary embodiment of the present disclosure.

Moreover, once the stitching portion is complete, the suture lock is used to secure the suture against the surgical site and complete the suturing process. As shown in FIG. 4, at the completion of the stitching process, the first end of the suture 135 is engaged with the end of the tube 105. Next, the first rod 110 may be retracted further into the tube 105 (e.g., retracted within the tube) to release the first end of the suture 135 from the end of the tube 105 and allow engagement with the second rod 115, as shown in FIG. 5. In particular, the retraction of the first rod 110 into the tube 105, that is, away from the end of the tube, causes the first end of the suture 135 to be attracted to the magnetic field of the second rod 115. The movement of the first rod 110 within the tube 105 may be controlled by a lever integrally formed on the tube, however, the present disclosure is not limited to the lever and another actuation device may be used to trigger the movement within the tube.

Figure 7:
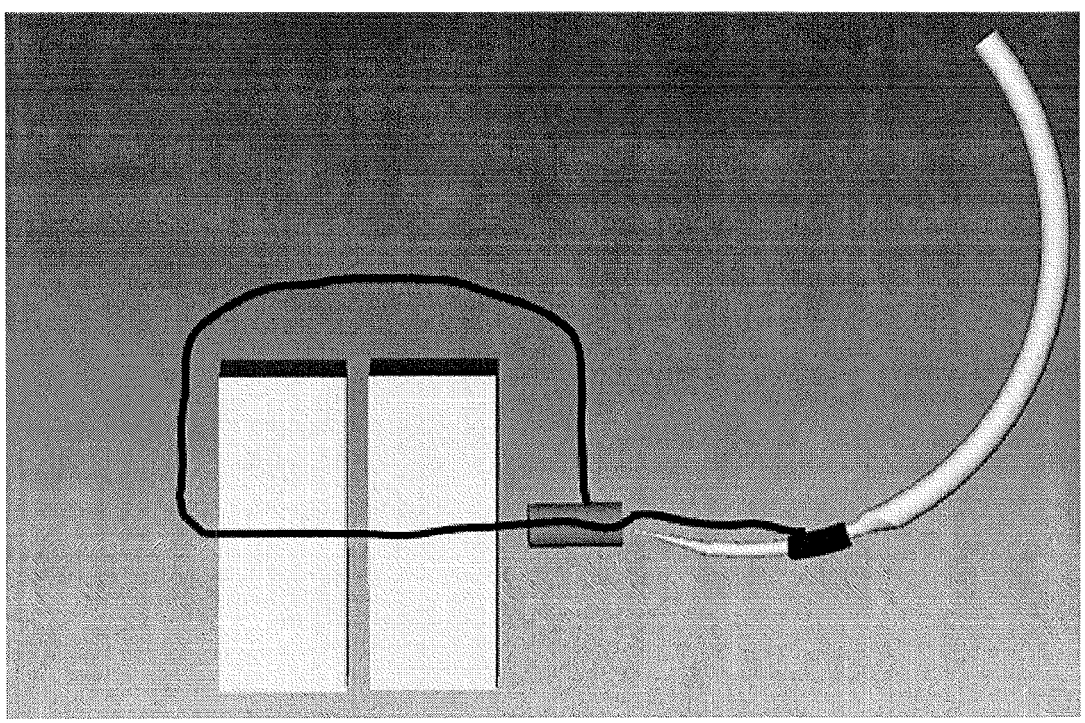
FIGS. 7 and 8 provide a more detailed illustration of the locking of the suture against a material according to an exemplary embodiment of the present disclosure.
Figure 8:
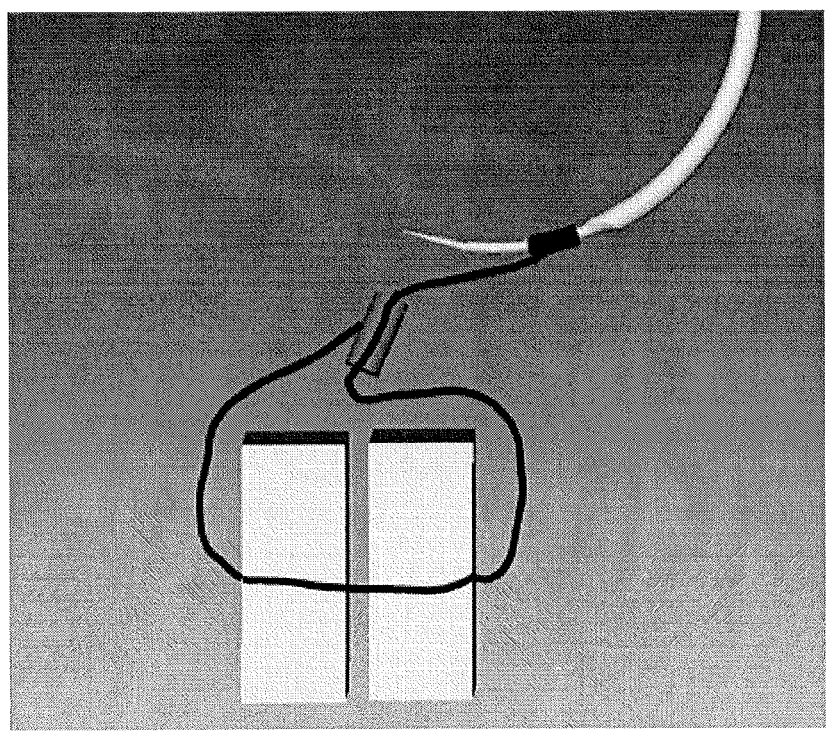

Once the first end of the suture 135 is engaged with the second rod 115 on which the suture lock 130 is mounted, the suturing system may be moved away from the material (the surgical site) which causes the needle to be removed from the material as well. Further, the movement of the suturing system 100 away from the material 140 also causes the suture lock 130 to slide over the first end of the suture 135 (attracted to the magnetic second rod) and eventually off of the second rod 115. The inner diameter of the suture lock 130 may be greater than the outer diameter of the first end of the suture 135 to allow the suture lock 130 to slide over the suture 135. As the suturing system 100 continues to be moved away from the material 140, the suture lock 130 moves to an abutting position against the surgical site to thus bind the material pieces together and also act as a knot to hold the suture in place. FIGS. 7 and 8 provide a more detailed illustration of the movement of the suture lock toward the surgical site as distance to the needle increases. A further description of the suture lock will be described herein below.

Figure 9:
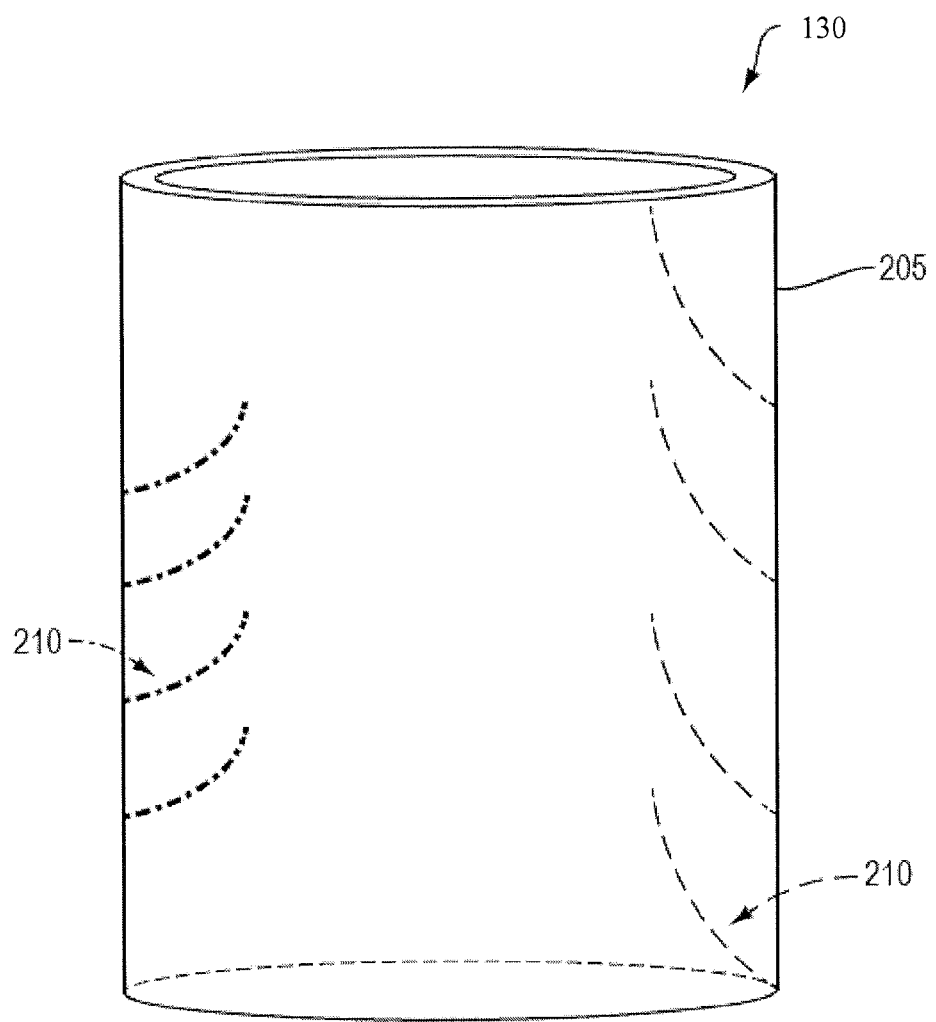
FIG. 9 illustrates a suture lock of the suturing system according to an exemplary embodiment of the present disclosure.

As shown in FIG. 9, the suture lock 130 may include a knotting tube 205 with a passageway formed therethrough and a plurality of protrusions 210 that extend from at least a portion of an inner surface of the tube 205 to pierce the suture within the passageway. The knotting tube in FIG. 9 is illustrated as a hollow cylindrical tube however; the present disclosure is not limited thereto. For example, the cross-sectional shape of the tube may be circular, rectangular, triangular, or the like. The knotting tube 205 itself may also be varied in length. Additionally, the protrusions 210 may be formed at merely a portion of the tube 205 to facilitate the cutting of the tube to a desired length. Alternately, the protrusions 210 may be formed along the entire inner surface of the knotting tube 205.

Figure 10:
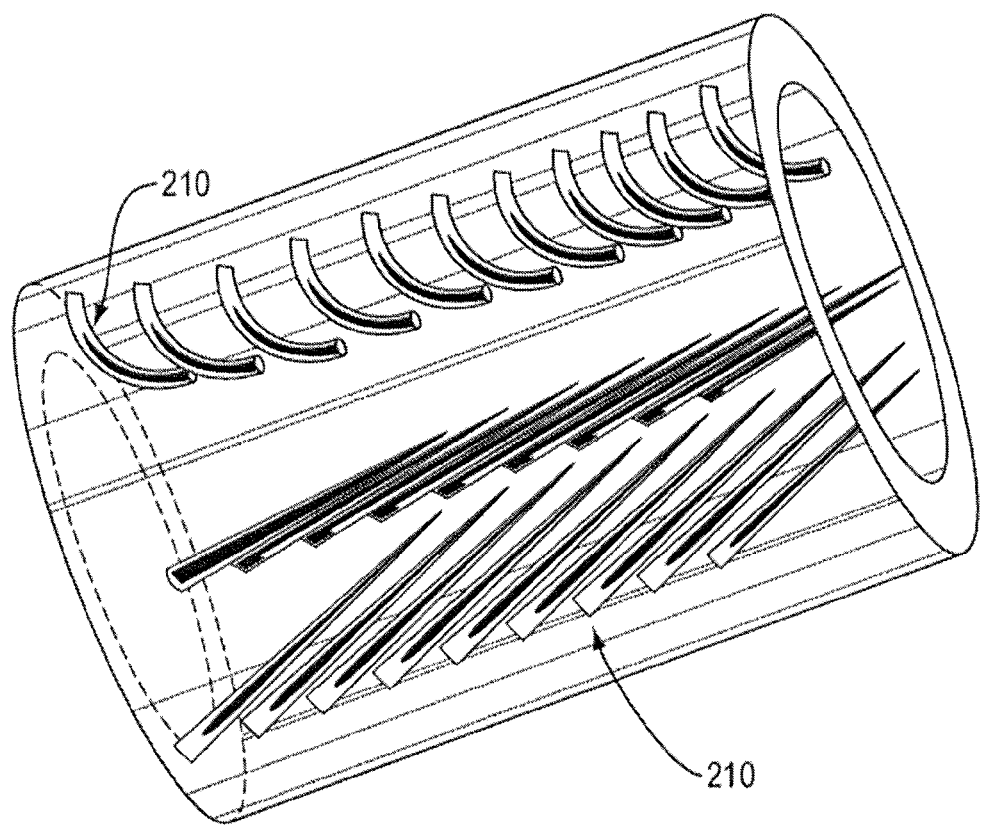
FIG. 10 illustrates the protrusions within a knotting tube of the suture lock according to an exemplary embodiment of the present disclosure.

Further, FIG. 10 illustrates details of the protrusions 210 within the knotting tube 205. As shown, the shape of the protrusions 210 may be varied. For example, the protrusions 210 may be curved, spiked, barbed, hooked, angled, straight, or the like without being limited to what is shown in FIG. 10. The protrusions 210 are also not limited in length and may be formed at varied lengths at an angle less than 90 degrees.

Figure 11:
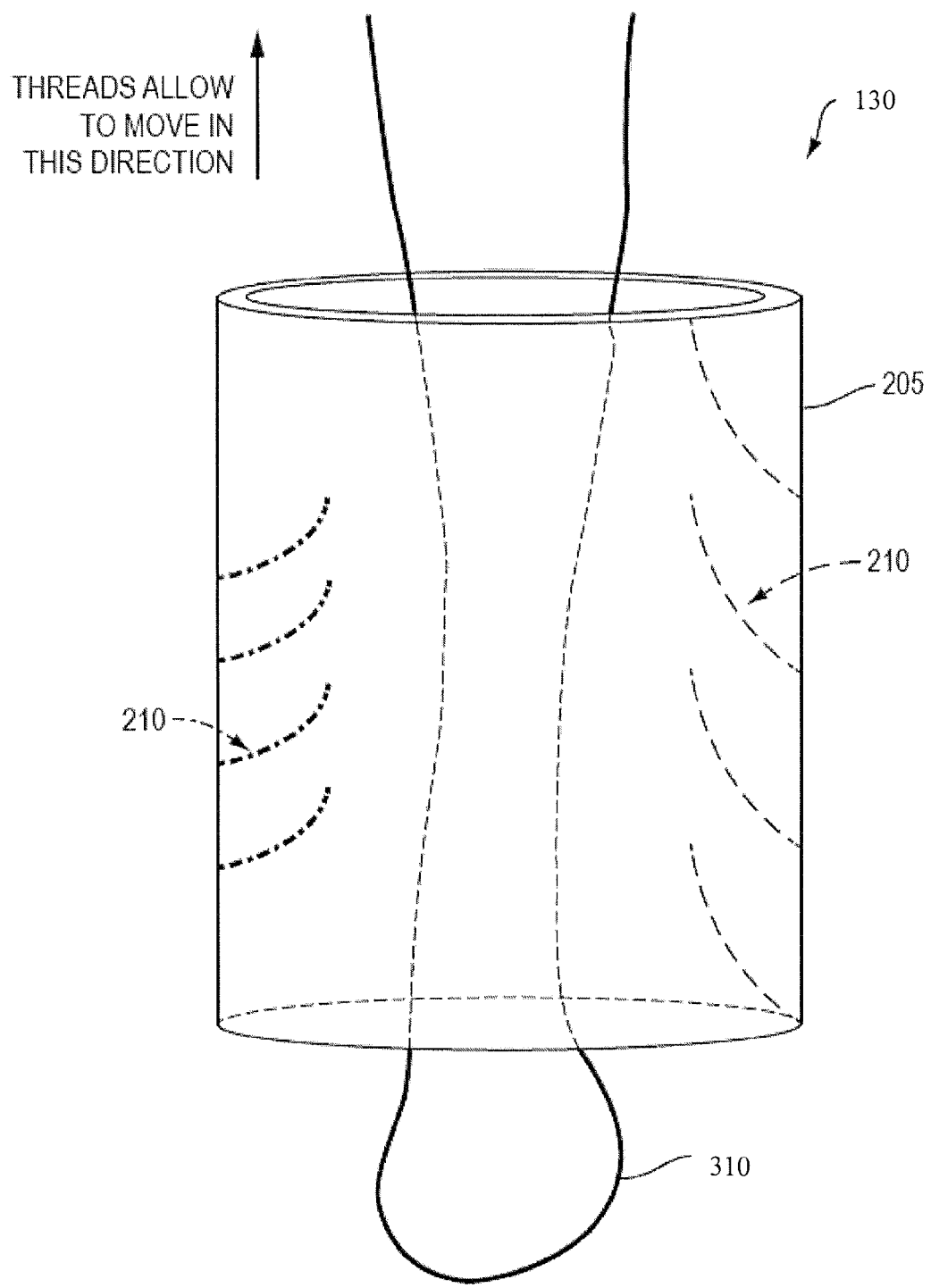
FIG. 11 illustrates a guiding loop passed through the knotting tube according to an exemplary embodiment of the present disclosure.

The particular angle of less than 90 degrees ensures that the protrusions 210 are capable of piercing or penetrating into the suture. In addition, the protrusions 210 may be formed as soft protrusions that are bendable as the suture passes through the knotting tube. The inner surface of the knotting tube 205 may also be formed with a rough topography to catch the suture as it passes therethrough. For example, the rough topography may have a smooth surface in the direction in which the suture enters into the passageway and a rough surface in the opposite direction to hold the suture in place by friction between the surfaces. Alternately, other Van der Waals formed friction mechanisms may be used to prevent the suture from moving in a backward direction According to one exemplary embodiment of the present disclosure, the suture lock 130 may also include a guiding loop 310 as shown in FIG. 11. The guiding loop 310 may be used to fix the second end of the suture 135 into the knotting tube 205 prior to commencing the suturing process. In particular, the guiding loop 310 may be used to pull the end of the suture 135 through the passageway of the knotting tube 205. That is, the guiding loop 310 may be pulled through the tube 205 to form a loop at one open end of the tube 205. The loop may then be used to pull the suture through passageway. The guiding loop 310 facilitates the insertion of the suture 135 into the tube 205 considering the narrow passageway that may be formed within the tube 205. The arrow shown in FIG. 11 indicates the pulling direction of the guiding loop 310 once the suture is wrapped around or attached in a manner to the loop of the guiding loop 310.

Figure 12:
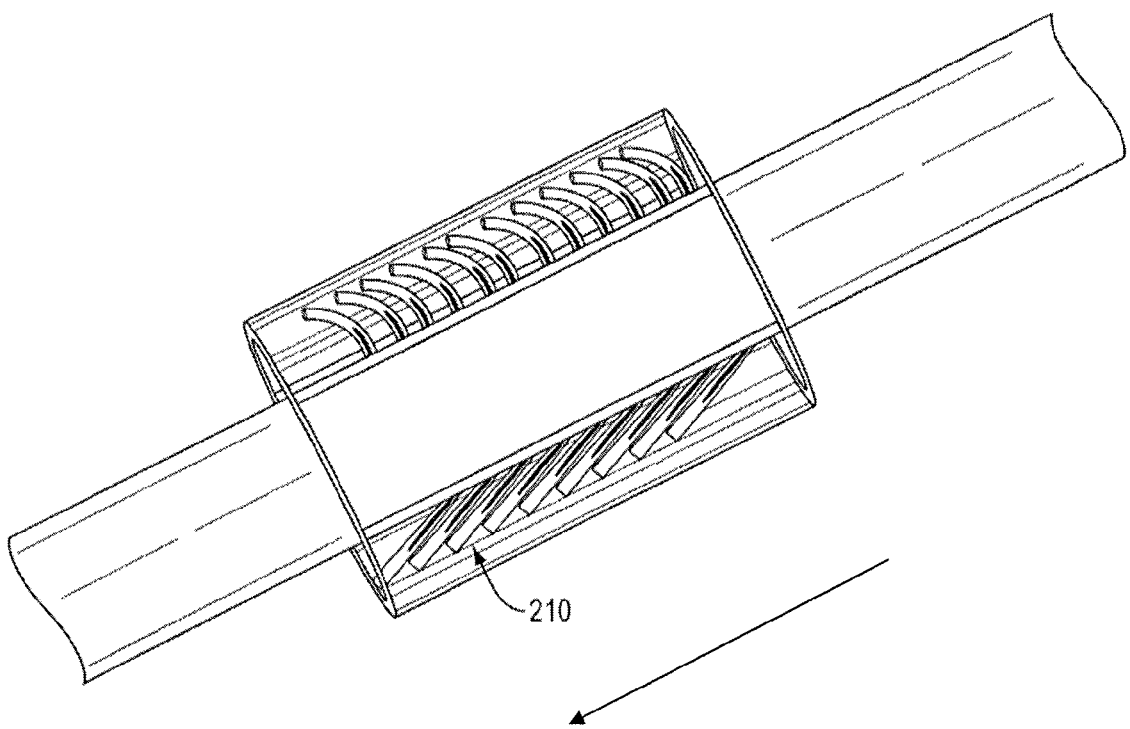
FIG. 12 illustrates the suture fixed within the suture lock according to an exemplary embodiment of the present disclosure.

Referring to FIG. 12, the arrow shown indicates a locking direction of the suture lock 130. In other words, when the suture pulled in the indicated direction, the protrusions 210 within the knotting tube 205 penetrate into the suture 135, thus locking or fixing the suture 135 within the tube. The suture lock 130 is first pushed in the opposite direction from the arrow to position the lock against the surgical site, and then would be unable to be released from such an abutting position due to the penetration of the protrusions 210. Accordingly, a knot tying step may be omitted while maintaining a strong and abutting connection between the suture and the surgical site. The suture lock supplies sufficient tension against the surgical site to provide a secure completion of the suturing process.

Figure 13:
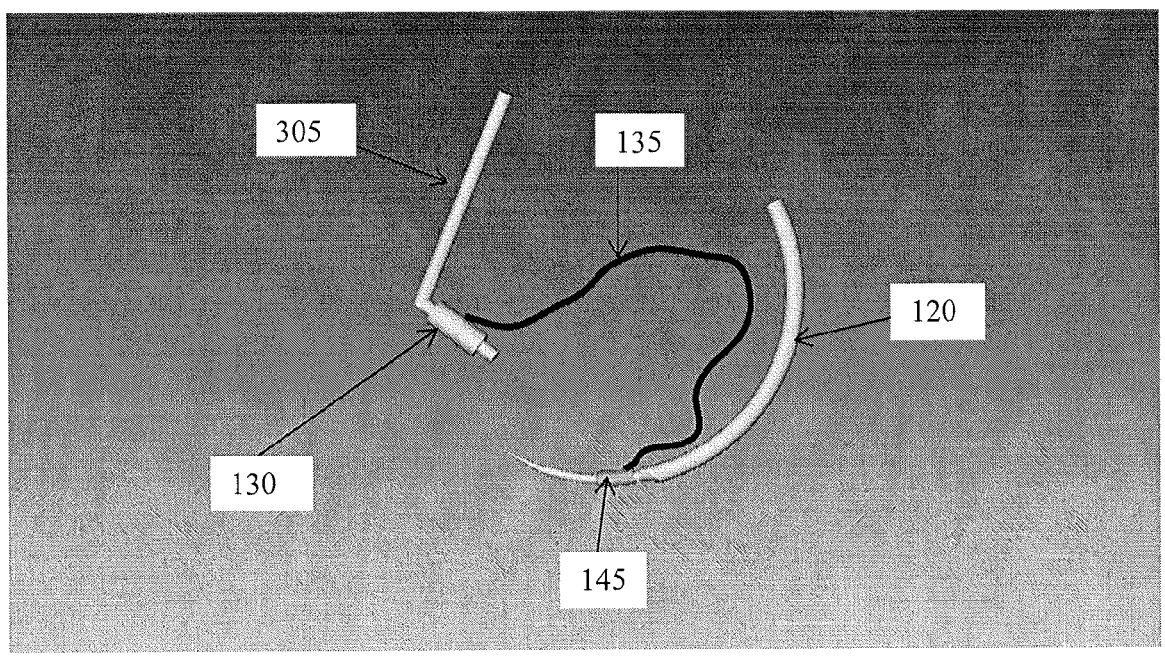
FIG. 13 illustrates a suturing system according to another exemplary embodiment of the present disclosure.

According to another exemplary embodiment of the present disclosure, the suturing system may be applied as a two-handed system that is still capable of improving the accuracy of a suturing process and also utilizing a suture lock to avoid requiring a manual knot tying securement. As shown in FIG. 13, the alternate embodiment includes a suturing system having a needle 120 that communicates with a forceps arm 305. A suture lock 130 may be mounted onto the forceps arm 305. Further, a first end of the suture 135 engages with the tip of the needle 120. As an example, FIG. 13 illustrates an embodiment in which the first end of the suture 135 includes a ring-shaped magnet 145. Further, the second end of the suture 135 engages with the suture lock 130, similar to the previously discussed embodiment.

Figure 14:
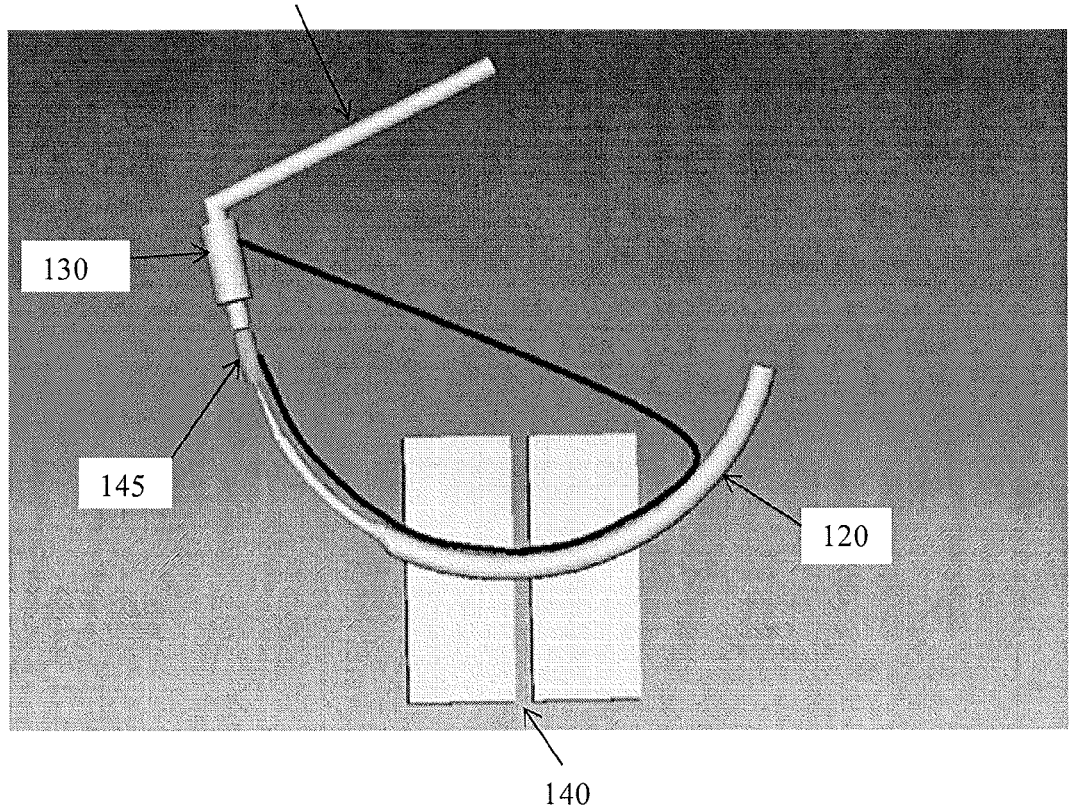
FIGS. 14 and 15 illustrate the operation of the suture system in FIG. 13 according to an exemplary embodiment of the present disclosure.
Figure 15:
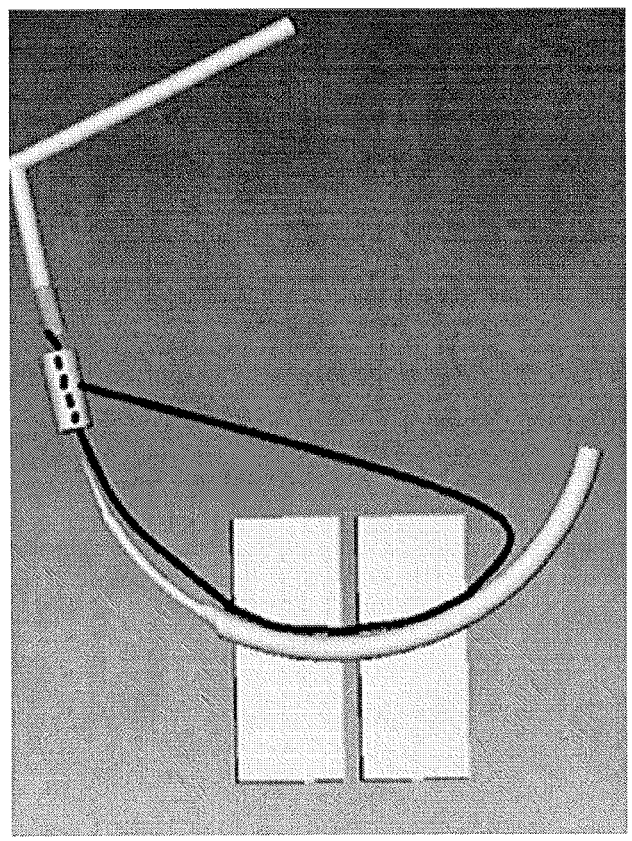

Furthermore, FIG. 14 illustrates the insertion of the needle 120 (an insertion portion thereof) and the first end of the suture 135 through a material 140. Upon piercing through the material, the first end of the suture 135 engages with the forceps arm 305. Similar to the embodiment discussed above, the forceps arm 305 and the first end of the suture 135 may be magnetic to thus engage with each other. Once the first end of the suture 135 is engaged with the forceps arm 305, the arm may be moved away from the needle 120 and the first end suture 135 to release the suture lock 130 therefrom, as shown in FIG. 15. The suture lock 130 has been described herein above and thus details thereof are omitted. Accordingly, the suture lock 130 may be positioned to abut the material 140 to fix the suture against a surgical site. This two-handed process may be applicable to surgical areas with minimal space constraints, as an example. The advantage of performing the stitching and employing the suture lock in this embodiment reduces the time required to execute the suturing process as well as increases the accuracy of fixing the suture against the surgical site.

Notably, the engagement of the suture with the needle and the tube as discussed herein is not limited to a magnetic configuration. For example, the suture engagement may be through a variety of attractive forces such as mechanical, magnetic, adhesive techniques, or the like that are capable of adjusting a magnetic field strength and direction. The above-described autotransfer technique in which the polarity is essentially reversed such that the suture is attracted and repelled during suture is merely exemplary. Alternately, electromagnetic coils may be used to engage and release the suture from the system. For example, an electric current may pass through the coil to generate a magnetic field. The use of the electromagnetic coil further increases the strength of the magnetic field. The system may also be operated using a power supply with one or more batteries. The power supply may be external to the system and the power electronics may be configured to control the flow of current to the electromagnet in one or more directions.

According to another aspect of the claimed disclosure, the suturing system may be integrated with a robotic arm to be operated remotely. In particular, the movement of the rod within the tube of the system may be actuated and controlled by a robotic arm operated by a user remotely from the site. Thus, the system may be applicable to medical procedures with substantial spatial constraints. For example, the suturing system may be applied to endoscopic or laparoscopic surgeries. However, the present disclosure is not limited to medical procedures but may also be applied to any field where multiple materials are being bound together. For example, the suturing system may be applied to a packaging technology, or the like.

As discussed, the suturing system integrated with a suture lock of the claimed disclosure is capable of reducing errors occurring during the process of suture tying while reducing training time for medical staff. The particular design of the knotting tube of the suture lock eliminates the need for complex techniques and external devices. The knotting tube may also be made of a material to encourage cell growth over the tube itself to absorb the tube. Accordingly, the knotting tube of the claimed disclosure provides a device capable of simplifying the process of suture tying for medical procedures. The suturing system also decreases the time required to perform suturing based on the simplification of the system and the ability to operate the system with one hand. Since the system eliminates the need for working with two separate instruments in both hands, the system is capable of more easily suturing in traditionally less accessible locations while also providing for more accurate suturing. Additionally, since the entire needle is not required to be pulled through a material, the risk of inadvertently puncturing neighboring tissue is substantially decreased. Lastly, the integration of the suturing system with a suture lock eliminates the requirement of two separate processes. That is, the two procedures are capable of being performed by one device which also improves the accuracy of the procedure and reduces human error.

The many features and advantages of the disclosure are apparent from the detailed specification, and thus, it is intended by the appended claims to cover all such features and advantages of the invention which fall within the true spirit and scope of the disclosure. Further, since numerous modifications and variations will readily occur to those skilled in the art, it is not desired to limit the invention to the exact construction and operation illustrated and described, and accordingly, all suitable modifications and equivalents may be resorted to, falling within the scope of the disclosure.

What is claimed is:

1. A suturing system, comprising:
a tube having a first rod movable therein;
a second rod coupled to an outer surface of the tube;
a needle coupled to an end of the tube and having an insertion portion; and
a suture lock inserted onto the second rod, the suture lock includes,
a knotting tube having a passageway formed therethrough; and
a plurality of protrusions extending from at least a portion of an inner surface of the knotting tube to pierce a suture,
wherein a first end of the suture engages with a tip of the needle or the tube,
wherein a second end of the suture is fixed within the suture lock,
wherein the insertion portion is engaged with the first end of the suture prior to insertion through a material, and
wherein the suture lock is moved to abut a surgical site.

2. The suturing system of claim 1, wherein the protrusions are deformable in one direction to fix the suture and maintain the knotting tube of the suture lock abutting the surgical site.

3. The suturing system of claim 1, wherein the suture is magnetically engaged with the tip of the needle or the tube.

4. The suturing system of claim 3, wherein the first end of the suture is magnetic, the first rod within the tube is magnetic, and the second rod coupled to the outer surface of the tube is magnetic.

5. The suturing system of claim 4, wherein a magnetic strength of the first rod is greater than a magnetic strength of the first end of the suture.

6. The suturing system of claim 4, wherein the first rod and the second rod have a same magnetic field direction and the first rod and the first end of the suture have an opposite magnetic field direction.

7. The suturing system of claim 6, wherein the first rod is pushed toward the end of the tube to release the first end of the suture from the tip of the needle and allow engagement with the end of the tube.

8. The suturing system of claim 7, wherein the first rod is retracted into the tube to release the first end of the suture from the end of the tube and allow engagement with the second rod.

9. The suturing system of claim 8, wherein the suturing system is pulled away from a surgical site to allow the first end of the suture to pass through the suture lock and fix the suture against the surgical site.

10. The suturing system of claim 9, wherein the movement of the first rod is controlled by a lever integrally formed on the tube.

11. A suturing method, comprising:
engaging a first end of a suture with a suture lock coupled to an outer surface of a tube having a first rod movable therein;
engaging a second end of the suture with a tip of a needle coupled to an end of the tube;

piercing an insertion portion of the needle and the second end of the suture through a material;

pushing the first rod toward the end of the tube to release the second end of the suture from the needle and to engage the second end of the suture with the end of the tube;

retracting the first rod back into the tube to engage the second end of the suture with a second rod on which the suture lock is disposed; and pulling the second end of the suture through the suture lock to fix the suture against the material, wherein the suture lock includes a knotting tube having a passageway formed therethrough and a plurality of protrusions extending from at least a portion of an inner surface of the tube to pierce the suture and fix the suture against the material and moving the suture lock to abut a surgical site.

12. The suturing method of claim 11, wherein the protrusions are deformable in one direction to fix the suture and maintain the knotting tube of the suture lock abutting the material.

13. The suturing method of claim 11, wherein the suture is magnetically engaged with the tip of the needle or the tube.

14. The suturing method of claim 13, wherein the first end of the suture is magnetic, the first rod within the tube is magnetic, and the second rod coupled to the outer surface of the tube is magnetic.

15. The suturing method of claim 14, wherein a magnetic strength of the first rod is greater than a magnetic strength of the first end of the suture.

16. The suturing method of claim 14, wherein the first rod and the second rod have a same magnetic field direction and the first rod and the first end of the suture have an opposite magnetic field direction.

17. The suturing method of claim 11, wherein prior to pulling the second end of the suture through the suture lock, the piercing of the insertion portion of the needle through the material, the pushing of the first rod toward the end of the tube, and the retracting of the first rod back into the tube are repeated.

18. The suturing method of claim 11, wherein the second end of the suture includes a magnetic bead inserted over the tip of the needle to engage therewith.

* * * * *